(12) United States Patent
Hornung et al.

(10) Patent No.: US 9,002,515 B2
(45) Date of Patent: Apr. 7, 2015

(54) MONITORING OF A MEDICAL DEVICE

(75) Inventors: Oliver Hornung, Fürth (DE); Donal Medlar, Weisendorf (DE)

(73) Assignee: Siemens Aktiengesellschaft, München (DE)

( * ) Notice: Subject to any disclaimer, the term of this patent is extended or adjusted under 35 U.S.C. 154(b) by 501 days.

(21) Appl. No.: 12/692,316

(22) Filed: Jan. 22, 2010

(65) Prior Publication Data

US 2010/0191371 A1 Jul. 29, 2010

(30) Foreign Application Priority Data

Jan. 28, 2009 (DE) .......................... 10 2009 006 417

(51) Int. Cl.
| | |
|---|---|
| *G05B 19/18* | (2006.01) |
| *G05B 15/00* | (2006.01) |
| *G01D 18/00* | (2006.01) |
| *A61B 6/08* | (2006.01) |
| *H05G 1/28* | (2006.01) |
| *A61B 6/00* | (2006.01) |

(52) U.S. Cl.
CPC ............... *A61B 6/583* (2013.01); *A61B 6/4441* (2013.01); *A61B 6/504* (2013.01); *A61B 6/547* (2013.01); *Y10S 901/47* (2013.01)

(58) Field of Classification Search
CPC .......... A61B 6/58; A61B 6/583; A61B 6/547; A61B 6/504; A61B 6/00
USPC .......... 700/245, 250, 253, 254, 259; 901/2, 9, 901/47; 378/163, 164, 196–198, 205–207; 356/139.06, 139.07, 139.08
See application file for complete search history.

(56) References Cited

U.S. PATENT DOCUMENTS

| | | | |
|---|---|---|---|
| 5,937,533 | A | 8/1999 | Meyer et al. |
| 6,050,725 | A | 4/2000 | Regimand |
| 6,079,876 | A | 6/2000 | Schuetz |
| 6,206,566 | B1 * | 3/2001 | Schuetz ........................ 378/205 |
| 6,267,502 | B1 * | 7/2001 | McNeirney et al. ........... 378/206 |
| 6,379,041 | B1 * | 4/2002 | Schuetz et al. ................ 378/205 |
| 2001/0053204 | A1 * | 12/2001 | Navab et al. .................. 378/205 |

(Continued)

FOREIGN PATENT DOCUMENTS

| | | |
|---|---|---|
| CN | 1137368 A | 12/1996 |
| DE | 19950793 A1 | 8/2000 |

OTHER PUBLICATIONS

Binder et al, "The Surgeon's Third Hand an Interactive Robotic C-Arm Fluoroscope", Mobile Robots, Towards New Applications, Edited by Aleksander Lazinica, pp. 404-418, Germany, Dec. 2006.*

(Continued)

*Primary Examiner* — Khoi Tran
*Assistant Examiner* — Abby Lin
(74) *Attorney, Agent, or Firm* — Lempia Summerfield Katz LLC

(57) ABSTRACT

The present embodiments relate to a monitoring system for a medical device, wherein the medical device comprises a robot and an image recording part which can be moved by the robot. Provision is made for a radiation source which is attached to the medical device, and for a radiation receiver which is situated remotely from the medical device and is for receiving radiation that is emitted from the radiation source. A comparison entity compares the point of impact of radiation on the radiation receiver with one or more predetermined points of impact of radiation on the radiation receiver. The invention further relates to a corresponding method for monitoring a medical device.

20 Claims, 3 Drawing Sheets

(56) References Cited

U.S. PATENT DOCUMENTS

| | | | |
|---|---|---|---|
| 2002/0044631 A1* | 4/2002 | Graumann et al. | 378/205 |
| 2002/0071101 A1* | 6/2002 | Horbaschek et al. | 353/28 |
| 2004/0073336 A1* | 4/2004 | Huang et al. | 700/245 |
| 2005/0058256 A1* | 3/2005 | Beimler et al. | 378/162 |
| 2005/0209778 A1* | 9/2005 | Inbar et al. | 701/213 |
| 2006/0010969 A1* | 1/2006 | Fox | 73/105 |
| 2006/0098851 A1* | 5/2006 | Shoham et al. | 382/128 |
| 2006/0109957 A1* | 5/2006 | Lutjens et al. | 378/205 |
| 2007/0174964 A1* | 8/2007 | Lemire et al. | 5/600 |
| 2008/0002871 A1* | 1/2008 | Gunzert-Marx et al. | 382/132 |
| 2008/0064952 A1* | 3/2008 | Li et al. | 600/424 |
| 2008/0107241 A1* | 5/2008 | Yatsenko et al. | 378/207 |
| 2008/0161684 A1* | 7/2008 | Li et al. | 600/426 |
| 2008/0285725 A1* | 11/2008 | Dehler | 378/207 |
| 2009/0149867 A1* | 6/2009 | Glozman et al. | 606/130 |
| 2009/0278702 A1* | 11/2009 | Graumann et al. | 340/686.2 |
| 2010/0228118 A1* | 9/2010 | Maschke | 600/424 |
| 2010/0246778 A1* | 9/2010 | Heigl et al. | 378/207 |

OTHER PUBLICATIONS

Meng et al, "Self-Calibration of Camera-Equipped Robot Manipulators", The International Journal of Robotics Research, vol. 20, No. 11, Nov. 2001, pp. 909-921.*

German Office Action dated Sep. 14, 2009 with English translation.
Chinese Office Action dated Feb. 18, 2013 for corresponding Chinese Patent Application No. 201010105858.6 with English translation.

* cited by examiner

MONITORING OF A MEDICAL DEVICE

This application claims the benefit of DE 10 2009 006 417.6 filed Jan. 28, 2009, which is hereby incorporated by reference.

BACKGROUND

The present embodiments relate to monitoring medical devices.

In various fields of medicine, such as in neuroradiology and general angiography, three-dimensional (3D) applications are used in which three-dimensional image data records of an examination object are generated by x-ray imaging. For the purpose of creating the 3D image data records, C-arm x-ray devices are utilized. C-arm x-ray devices allow different projections to be recorded using a large-surface detector. Together with the opposing x-ray tube, the large-surface detector rotates about the examination object on at least a section of a circular trajectory. Using such C-arm systems, which can be utilized during interventions for intraoperative imaging in the field of angiography, it is possible by suitable kinematics and motion sequences to obtain data for the creation of computer tomography images. In order to move the C-arm in predefined trajectories around the recording object, the C-arm movement can be effected by a robot. This applies in the case of the "Axiom Artis zeego" C-arm system produced by Siemens, for example.

In order to ensure high-quality reconstruction of the recorded images, knowledge of the actual trajectory followed by the C-arm during the scan is needed. It must be possible to reproduce, with a high degree of precision, the trajectories used for the reconstruction.

SUMMARY AND DESCRIPTION

The present embodiments may obviate one or more of the drawbacks or limitations inherent in the related art. For example, a monitoring system for a medical device and a corresponding method which allow the precision of the movements of a medical device to be checked are provided.

In one embodiment, the monitoring system relates to a medical device including a robot and an image recording part which can be moved by the robot. The monitoring system has a radiation source that is attached to the medical device, and a radiation receiver that is situated remotely from the medical device. The radiation receiver is used to receive the radiation emitted by the radiation source. The medical device may include a comparison entity for comparing a point of impact of radiation on the radiation receiver with one or more predetermined points of impact of radiation on the radiation receiver.

The medical device is constructed such that the image recording part is suitably connected to the robot. Movements of the image recording part can be effected by movements of the robot. The radiation source is attached to the medical device. The radiation source can be attached to the robot and/or the image recording part. As a result of moving the robot or the image recording part, the radiation source is also moved. If the radiation source emits a beam, the position of the beam changes in space as a result of a movement of the robot or of the image recording part.

In addition to the radiation source, the monitoring system has a radiation receiver. This is not attached to the medical device, but is remotely situated relative thereto. Unlike the radiation source, the radiation receiver may not be correspondingly moved by a movement of the robot. The radiation receiver may be attached to the wall of the room in which the medical device is located, for example. The radiation receiver is positioned such that, at least in many configurations of the robot or in the corresponding orientations of the image recording part, radiation from the radiation source arrives at the radiation receiver and can be detected thereby.

The radiation receiver may include a two-dimensional resolution. The location at which the radiation hits (strikes) the radiation receiver may be identified. Accordingly, the actual point of impact of radiation on the radiation receiver may be compared with a specific predetermined point of impact. This actual point of impact may be derived by analyzing or processing data that is detected by the radiation receiver. An averaged value may be used as a point of impact, for example, the central area of a field of impact.

The comparison entity may be part of the radiation receiver. Alternatively, the comparison entity can also be part of the medical device or another entity. In this case, data transfer takes place from the radiation receiver to the medical device or the other entity.

The radiation source may be a laser. Various types of laser will allow meaningful results to be obtained by the comparison entity. For example, the radiation emitted by the laser does not have to be circular in cross section.

The radiation receiver may be a camera. This preferably offers high resolution, for example, in the megapixel range.

The image recording part may be a C-arm x-ray device. However, the image recording part is not restricted to this, and is also suitable for other types of image-recording apparatus moved by a robot.

In one embodiment, the robot has freedom of movement in the six directions of a Cartesian system of coordinates. The attachment point between the robot and the image recording part, and hence the image recording part, may move freely in three-dimensional space in this case.

The comparison entity may output a notification if the point of impact deviates from the one or more predetermined points of impact. The output may be an error notification or an alarm, for example. The notification can be optical, for example, by an indication on a display, or acoustic, for example, by a warning tone. The notification may cause functions of the image recording part to be disabled. In the case of x-ray imaging, for example, the patient should not be exposed to any radiation that produces unusable results.

The predetermined point of impact or points of impact can consist of a specific point of impact and an associated tolerance range. For example, the predetermined point of impact can be a circle of possible points of impact around a central point.

A method may be used for monitoring a medical device. The medical device may include a robot and an image recording part which can be moved by the robot. Radiation is emitted from a radiation source which is attached to the medical device. The radiation emitted by the radiation source is received by a radiation receiver which is situated remotely from the medical device. The point of impact of the received radiation on the radiation receiver is compared with one or more predetermined points of impact of radiation on the radiation receiver.

The above explanations relating to the monitoring system and/or device and the embodiments and developments apply correspondingly to a method for monitoring. The same applies correspondingly to a monitoring system and/or device in respect of the embodiments and developments of the method explained below.

In one embodiment, following a notification due to a deviation of the point of impact from the one or more predetermined points of impact, a calibration of the robot takes place. The presence of the notification must be taken to indicate that the movement of the robot or of the image recording part was other than as predicted. The predetermined point or points of impact correspond to the prediction. In order to reorganize the movement in accordance with the prediction, the robot is calibrated. This calibration may include all variety of acts and measures; the actual embodiment depends on the construction and functionality of the robot.

The robot may be moved into a first predetermined configuration and a comparison is then made of the point of impact with one or more predetermined first points of impact. A configuration of the robot corresponds to a specific state of the robot and hence a specific spatial position of the image recording part. When this position has been adopted, the radiation source emits radiation and it is verified whether the radiation receiver receives the radiation at a point of impact associated with the first configuration. If the robot kinematics are functioning correctly or if the system is correctly modeled, no deviation or no significant deviation should be found.

Following the first configuration, the robot may be moved into a second predetermined configuration and a comparison is then made of the point of impact with one or more predetermined second points of impact. Two or more configurations can be scanned in this way in order to ensure a thorough check of the robot movements.

The first point or points of impact may be same as the second point or points of impact. If the robot has multiple degrees of freedom of movement, in particular, there is generally a multiplicity of configurations which result in the same point of impact on the radiation receiver of the radiation from the radiation source. Alternatively, the predetermined first and second point or points of impact may differ.

The predetermined point or points of impact, with which the point of impact of the radiation is compared, may be specified in advance with reference to parameters of the robot. Parameters of the radiation source and of the radiation receiver can also be taken into consideration for this purpose. For example, a parameter model could be used where a specific combination of these parameters corresponds to each system configuration. Specific parameters may be utilized in the model. Accordingly, the point at which the radiation hits the receiver may be calculated.

It is advantageous if the method is carried out outside of the routine operation of the medical device. The emission of radiation by the radiation source and/or the detection and checking of the point of impact on the radiation receiver is therefore suspended when images are being recorded by the medical device. The routine operation of the medical device therefore takes place at a separate time from its checking.

DETAILED DESCRIPTION

Figure 1:
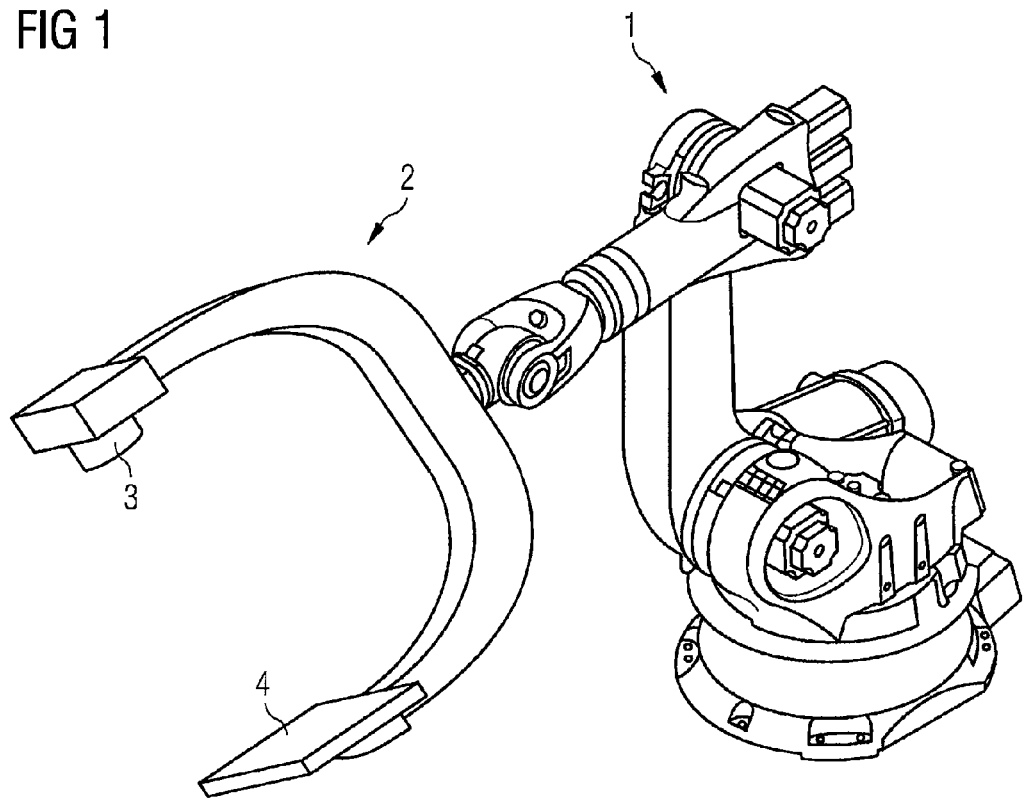
FIG. 1 shows one embodiment of an x-ray system.

FIG. 1 is a schematic illustration of an x-ray facility (system) in the form of a C-arm x-ray device. The C-arm 2 of the x-ray facility is guided by an articulated-arm robot 1. The C-arm 2 is coupled to the robot hand of the robot 1 and can be moved around a patient by the robot hand on a path of travel that can be predetermined. The robot arm allows the movement of x-ray source 3 and x-ray detector 4 on a defined trajectory around the patient. By virtue of the construction of the articulated-arm robot 1, the C-arm 2 can be moved freely in space with six degrees of freedom. In other words, the C-arm 2 can be moved and transported flexibly in any desired direction in space and in any desired direction and position relative to a patient. Such an x-ray facility is suitable for angiography applications, for example.

During operation of the x-ray facility, image sequences are recorded over precisely defined trajectories of the C-arm 2. Using the data that has been recorded, an image of the patient can be reconstructed by suitable algorithms. In order to obtain a high reconstruction quality of the image, the time-dependent position of the C-arm 2 corresponds precisely to the predetermined trajectory. A robot 1 that is equipped with kinematics of high absolute precision should be utilized accordingly. In order to achieve this precision, thorough calibration of the parameters of the kinematic and dynamic model is required. These parameters, subsequently referred to as system parameters, correspond to those of the robot 1 and C-arm 2 and include, for example, geometric relationships and rigidity. If the system parameters are known, the robot 1 can be controlled in such a way that the C-arm 2 moves precisely according to a predetermined trajectory.

However, it is also possible to use robots without absolute precision, in which case at least relative precision (i.e. repeat accuracy) should be available.

The system parameters are usually determined by the manufacturer in the context of calibration after the manufacture of the robot 1, and communicated to the operator of the x-ray facility. The robot 1 may be an absolute-precision positioning entity. It may be problematic that the system parameters can change over time. This is caused by, for example, wear, settlement effects, temperature changes and collisions. Of importance to the consistency of the system parameters is the sudden halting of the robot 1, for example, due to use of the emergency-off switch, where strong forces act due to the considerable weight of the robot 1.

If the system parameters change, the actual trajectory of the C-arm 2 deviates from the calculated trajectory. The image quality is degraded as a consequence. It may be taken into consideration that, as a result, the patient is exposed to a radiation dose which is unnecessary.

Therefore recalibration should take place occasionally. The time interval between these essential recalibrations is crucial for quality assurance but is completely unclear because no empirical data is available for this purpose, i.e. the time of occurrence of the cited effects is often unpredictable. In particular, it is not possible to draw on any experience relating to industrial robots which are moved continuously, as opposed to the robot 1 which only executes movements from time to time.

The more degrees of freedom the robot 1 or C-arm 2 has in movement, the more drastic the effects of a change in the system parameters. If movement only takes place along one axis, it is possible to compensate for errors using suitable algorithms. This can be done, for example, by recording the image of a known phantom and comparing it with the image that is to be expected when the movement of the C-arm 2 is correct, for example, corresponds to the calculation. However, such error correction and compensation may only be possible within a limited range. These methods may fail if the robot 1 has multiple degrees of freedom of movement and hence possible clear deviation from the predetermined trajectory.

Figure 2:
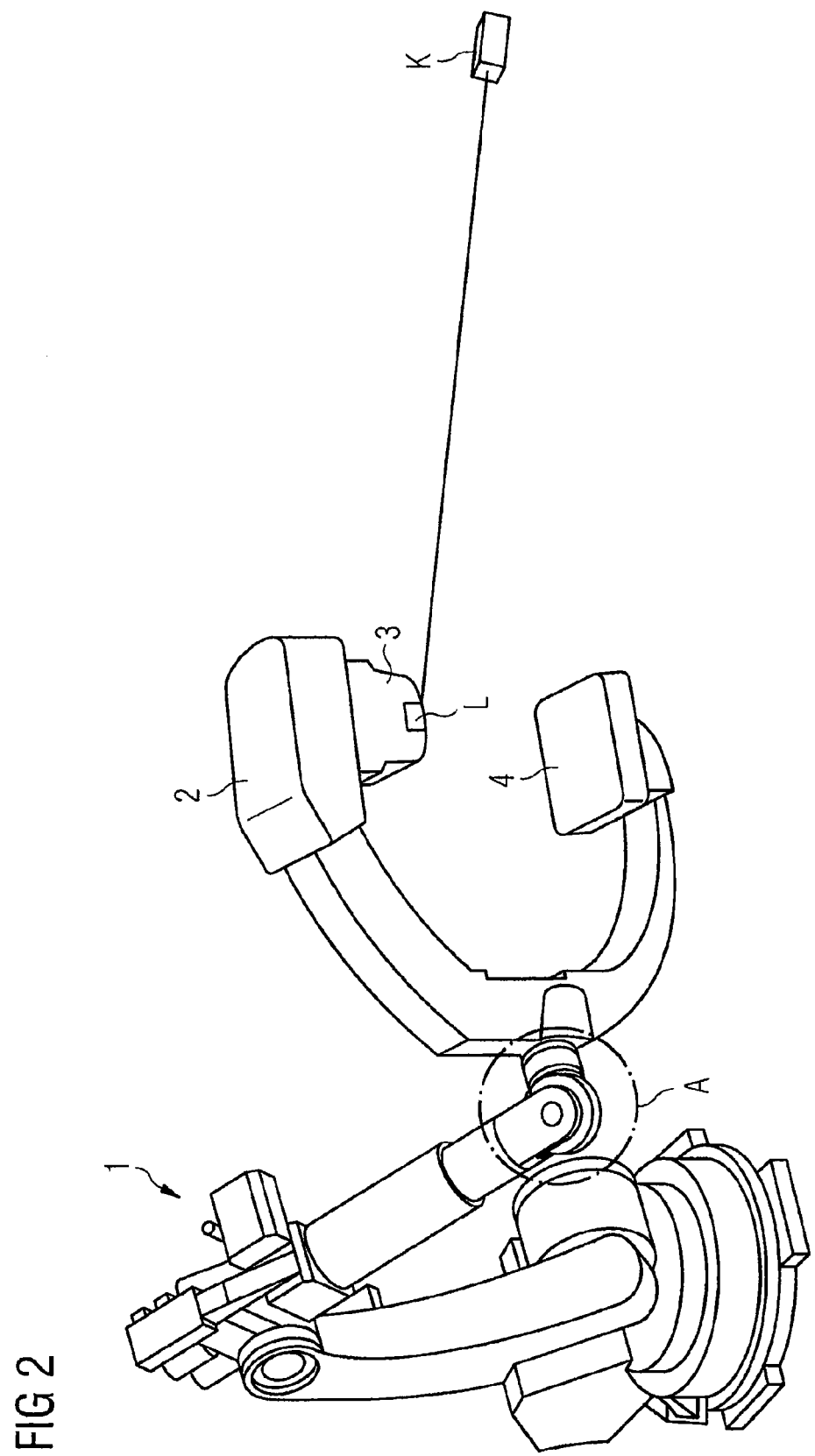
FIG. 2 shows one embodiment of an x-ray system and a monitoring system.

FIG. 2 shows the x-ray facility from FIG. 1 with a monitoring system. The monitoring system may include a camera K and a laser L. While the camera K is attached at a fixed location in the room containing the x-ray facility, the laser L is attached to a mobile part of the x-ray facility. FIG. 2 shows the case in which the laser L is fixed onto the C-arm 2 in the vicinity of the x-ray source 3. Alternatively, other positions are also possible and advantageous, for example, in the region 5 denoted by A.

Figure 3:
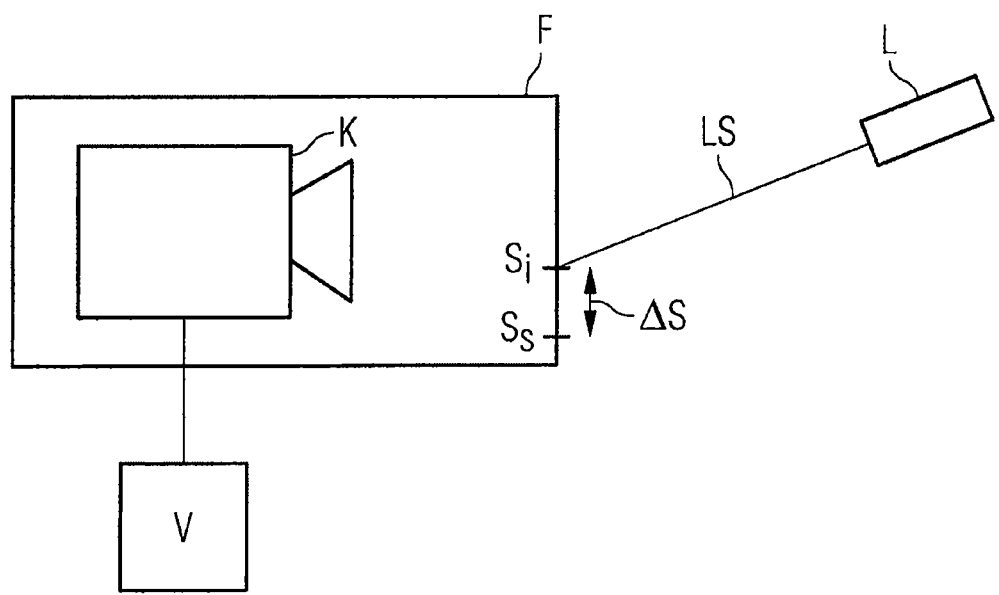
FIG. 3 shows one embodiment of a monitoring system.

The principle of the functionality of the monitoring system is explained with reference to FIG. 3. The beam LS of the laser L hits the point of impact $S_i$ on a surface F which is scanned by the camera K. In order to obtain sufficiently good resolution, a high-resolution camera K, for example, a megapixel camera, is used. The sensitive field of the camera K, which is hit by the laser beam LS according to the projection of the laser beam LS onto the surface F, may include a plurality of associated pixels. A mathematical approximation of this construct as a circle or ellipsis, the center of the construct can be specified. This makes it possible with subpixel precision to determine the current projection, the actual-projection $S_i$, of the laser beam LS onto the camera K. The precision may be increased by averaging over time. This involves the use of a static measuring method, in which the robot 1 is not moved for a short time during the measurement, such that the laser L maintains a constant position. The pixel noise of the camera K is eliminated by averaging the centers during this time.

If the system parameters of the system comprising robot 1 and C-arm 2, the parameters of the laser L (e.g. its beam orientation), and the position of the camera K relative to the robot 1 are known, it is possible to calculate, for each robot configuration or joint configuration of the robot 1, which projection the laser beam LS will assume on the camera K. Such a calculated projection is denoted as reference-projection $S_s$ in FIG. 3.

For the purpose of checking whether the system parameters have changed, a specific robot configuration or robot joint configuration may be adopted and the actual-projection $S_i$ may be compared with the calculated reference-projection $S_s$ which corresponds to this robot configuration. If there is a difference, the system parameters have changed and recalibration of the robot 1 may take place.

In the case of modeling imprecisions, in other words, in the event that not all system parameters are known exactly, the activation of a specific combination inevitably results in the actual-projection $S_i$ not corresponding precisely to the reference-projection $S_s$. This also applies to the case in which the calculation model contains different or fewer parameters than may be present. The latter corresponds to the existence of non-modeled influences. The deviation may be considered as a measure for the quality of the system model that is currently being used. The image-point deviation, which is caused by the imperfect system model and denoted by $\Delta S$ in FIG. 3, should be included in the analysis. A circle having the radius $\Delta S$ around the reference-projection $S_s$ may be defined as the tolerance range. The size of the circle may be determined from a multiplicity of measurements and the use of suitable statistical methods. Provided the actual-projection $S_i$ remains within the tolerance range, sufficient correspondence between actual-projection $S_i$ and reference-projection $S_s$ can be assumed.

As explained above, the camera K is permanently installed in the room containing the x-ray facility. Because the x-ray facility and the camera K are not connected together, the relative position of laser L and camera K is not precisely known at first. However, calculation of a reference-projection $S_s$ requires the knowledge of the system parameters and the knowledge of this relative position of camera K and laser L. The relative position of the camera K be is determined when the monitoring system is installed. For this purpose, a plurality of robot configurations are selected and the position of the associated projections is specified from an initial assumption of the camera position. The required relative position may be determined on the basis of the variations and the balancing of measurement and calculation by adapting the parameters of the model.

Using the monitoring system described above, a quality test maybe carried out by comparing actual-projection $S_i$ and reference-projection $S_s$. This does not take place during normal operation of the x-ray facility. Instead, specific robot configurations are selected at specific times, for example, once daily before the x-ray facility becomes operational. These robot configurations are preferably specified in advance in such a way that they result in the same reference-projection $S_s$ in each case. As a result of the multiplicity of degrees of freedom of movement of the robot 1, the same reference-projection $S_s$ can be achieved using the widest variety of robot configurations. Accordingly, even using a single reference-projection $S_s$, it is possible to check all system parameters. Alternatively, it is also possible to use robot configurations having different reference-projections $S_s$.

After selecting the relevant robot configuration, actual-projection $S_i$ and reference-projection $S_s$ are compared with each other. If the tolerance range explained above is not exceeded, this produces a positive result of the quality test. The system parameters have not changed significantly. This comparison takes place for a plurality of robot configurations, in order to ensure that none of the system parameters have undergone a significant change.

The comparison of actual-projection $S_i$ and reference-projection $S_s$ is done by a comparison entity V. The comparison entity V receives, via a suitable interface, the data which has been recorded and possibly already processed by the camera. The comparison entity V can be an independent apparatus. However, the comparison entity V can also be a part of another entity, for example, it can be integrated in the control unit of the robot 1.

The same robot configuration is preferably tested each time a check is performed. In this case, there exists a fixed set of combinations which has been defined for testing purposes. Alternatively, however, it is also possible to use varying robot configurations. For example, robot configurations which are particularly suitable for checking one or more specific system parameters can be used, such that attention can be focused on the consistency of specific system parameters according to the requirement and the current situation.

If a deviation exceeding the tolerance range is found between actual-projection $S_i$ and reference-projection $S_s$, the monitoring system may output a warning, automatically. This is intended to indicate to the person responsible for the x-ray facility that use of the device should not continue until the robot 1 is recalibrated.

The described monitoring system is characterized by a high level of precision. By virtue of using a megapixel camera, it is possible to detect deviations in the μm range. This high level of precision also allows the implementation of a progressive warning system, such that recalibration in the near future is indicated in the case of a slight deviation, a clear alarm is given in the case of an average deviation, and activation of the x-ray facility is automatically disabled in the case of a significant deviation.

The described monitoring system is economical to implement. For example, both the camera K and the laser L are low-cost components which are commercially available.

Finally, the described monitoring system has modest space requirements. Neither the x-ray facility nor the room containing the x-ray facility requires great modification.

The invention has been described above with reference to an exemplary embodiment. It is understood that numerous changes and modifications are possible without departing from the scope of the invention.

Various embodiments described herein can be used alone or in combination with one another. The forgoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. A monitoring system for a medical device, the medical device comprising a robot and an image recording part that is moveable by the robot, the monitoring system comprising:
   a radiation source that is attached to the medical device;
   a radiation receiver that is situated remotely from the medical device and is configured to receive radiation emitted from the radiation source; and
   a comparison entity configured to compare only a single point of impact of radiation on the radiation receiver with a predetermined point of impact of radiation on the radiation receiver and determine whether the point of impact of radiation on the radiation receiver is within a tolerance range associated with the predetermined point of impact of radiation on the radiation receiver based on the comparison,
   wherein the radiation source is a laser, and the radiation receiver is a camera, the laser and the camera being arranged such that the laser is configured to emit a laser beam towards the camera.

2. The monitoring system as claimed in claim 1, wherein the image recording part is a C-arm-x-ray device.

3. The monitoring system as claimed in claim 1, wherein the robot has freedom of movement in six directions of a Cartesian system of coordinates.

4. The monitoring system as claimed in claim 1, wherein the comparison entity is operable to output a notification when the point of impact deviates from the predetermined point of impact by more than the associated tolerance range.

5. The monitoring system as claimed in claim 1, wherein the one or more predetermined points of impact include a specific point of impact and an associated tolerance range.

6. The monitoring system as claimed in claim 1, wherein the comparison entity is operable to define the tolerance range to be a circle having a radius around the predetermined point of impact.

7. A method for monitoring a medical device comprising a robot, an image recording part that is movable by the robot, and a radiation source operable to emit radiation, the method comprising:
   receiving radiation emitted from the radiation source by a radiation receiver that is situated remotely from the medical device, wherein the radiation source is a laser, and the radiation receiver is a camera, the laser and the camera being arranged such that the laser is configured to emit a laser beam towards the camera;
   comparing only a single point of impact of the received radiation on the radiation receiver with a predetermined point of impact of radiation on the radiation receiver; and
   determining whether the point of impact of the received radiation on the radiation receiver is within a tolerance range associated with the predetermined point of impact of radiation on the radiation receiver based on the comparing.

8. The method as claimed in claim 7, wherein the image recording part is a C-arm-x-ray device.

9. The method as claimed in claim 7, wherein the robot has freedom of movement in six directions of a Cartesian system of coordinates.

10. The method as claimed in claim 7, further comprising outputting a notification when the point of impact deviates from the predetermined point of impact by more than the associated tolerance range.

11. The method as claimed in claim 10, wherein the notification is followed by calibration of the robot.

12. The method as claimed in claim 7, further comprising moving the robot into a first predetermined configuration,
    wherein comparing the point of impact with the predetermined point of impact comprises comparing the point of impact with one or more predetermined first points of impact after moving the robot into the first predetermined configuration.

13. The method as claimed in claim 12, further comprising moving the robot into a second predetermined configuration after moving the robot into the first predetermined configuration,
    wherein comparing the point of impact with the predetermined point of impact comprises comparing the point of impact with one or more predetermined second points of impact after moving the robot into the second predetermined configuration.

14. The method as claimed in claim 13, wherein the one or more predetermined first points of impact correspond to the one or more predetermined second points of impact.

15. The method as claimed in claim 13, wherein the one or more predetermined first points of impact differ from the one or more predetermined second points of impact.

16. The method as claimed in claim 7, further comprising specifying the predetermined point of impact in advance with reference to parameters of the robot.

17. The method as claimed in claim 7, wherein the receiving and the comparing are performed outside of routine operation of the medical device.

18. The method as claimed in claim 7, wherein the comparing comprises:
    determining a deviation between the point of impact of the received radiation on the radiation receiver and the predetermined point of impact of radiation on the radiation receiver; and
    comparing the determined deviation with the associated tolerance range.

19. The method as claimed in claim 18, further comprising notifying a user that the robot is to be recalibrated when the determined deviation exceeds the associated tolerance range.

20. The method as claimed in claim 19, wherein the notifying comprises automatically outputting, with a monitoring system, a warning in response to the determined deviation exceeding the associated tolerance range.

* * * * *